United States Patent
Hermens et al.

(10) Patent No.: US 6,723,524 B1
(45) Date of Patent: Apr. 20, 2004

(54) IMMUNOASSAY METHOD AND KIT

(75) Inventors: Willem Theodoor Hermens, Gronsveld (NL); Markus Robers, Marburg (DE); Cornelis Erik Hack, Diemen (NL); Lucien Adrianus Aarden, Broek in Waterland (NL)

(73) Assignee: Nederlandse Organisatie voor toegepastnatuurwetenschappelijk Onderzoek TNO, Delft (NL)

( * ) Notice: Subject to any disclaimer, the term of this patent is extended or adjusted under 35 U.S.C. 154(b) by 0 days.

(21) Appl. No.: 09/583,416

(22) Filed: May 31, 2000

Related U.S. Application Data

(63) Continuation of application No. PCT/NL98/00670, filed on Nov. 25, 1998.

(30) Foreign Application Priority Data

Dec. 1, 1997 (EP) ............................................. 97203758

(51) Int. Cl.⁷ ...................... G01N 33/53; G01N 33/543
(52) U.S. Cl. ...................... 435/7.92; 435/7.1; 435/7.79; 435/7.9; 435/28; 435/176; 435/188; 435/287.2; 435/288.3; 435/288.7; 435/808; 435/810; 436/172; 436/173; 436/524; 436/525; 436/527; 436/539; 436/808; 422/82.07; 422/82.08; 422/82.11; 310/311; 310/312; 310/323.16; 310/361; 310/369; 310/370; 310/371
(58) Field of Search ................................. 310/311, 312, 310/323.16, 361, 369, 370, 371; 422/82.07, 82.08, 82.11; 435/7.1, 7.72, 7.9, 7.92, 28, 176, 188, 287.2, 288.3, 288.7, 808, 810; 436/172, 173, 524, 525, 527, 539, 808

(56) References Cited

U.S. PATENT DOCUMENTS

| | | | | |
|---|---|---|---|---|
| 4,236,893 A | * | 12/1980 | Rice ......................... | 23/230 B |
| 4,242,096 A | * | 12/1980 | Oliveira et al. ............ | 23/230 B |
| 5,030,555 A | * | 7/1991 | Clemmons ..................... | 435/5 |
| 5,364,797 A | * | 11/1994 | Olson et al. ................ | 436/501 |
| 5,418,136 A |   | 5/1995 | Miller et al. ................... | 435/5 |
| 5,494,829 A | * | 2/1996 | Sandstrom et al. ......... | 436/518 |
| 5,656,448 A | * | 8/1997 | Kang et al. ................. | 435/7.94 |
| 5,656,504 A | * | 8/1997 | Johansson et al. .......... | 436/518 |
| 5,705,399 A | * | 1/1998 | Larue ........................... | 436/501 |
| 5,763,191 A | * | 6/1998 | Knoll et al. .................. | 435/7.1 |
| 5,922,550 A | * | 7/1999 | Everhart et al. ............ | 435/7.21 |
| 6,033,913 A | * | 3/2000 | Morozov et al. ............. | 436/86 |
| 6,355,429 B1 | * | 3/2002 | Nygren et al. ............... | 356/364 |

FOREIGN PATENT DOCUMENTS

| | | |
|---|---|---|
| EP | 0 368 462 A | 5/1990 |
| EP | 0 393 868 A | 10/1990 |
| EP | 0 458 231 A | 11/1991 |
| EP | 0 546 222 A1 | 6/1993 |

OTHER PUBLICATIONS

Speijer et al. Critical Micelle Concentrations and Stirring are Rate–Limiting in the Loss of Lipid mass during Membrane Degradation by Phospholidase A2. Biophysical Journal. (1996) vol. 70, pp. 2239–2247.*

Corsel et al., "The Role of Intrinsic Binding Rate and Transport Rte in the Adsorption of Prothrombin, Albumin, and Fibrinogen to Phospholipid Bilayers," *J. Colloid and Interface Science*, 111(2):544–554 (1986).

Cuypers et al., "The Adsorption of Prothrombin to Phosphatidylserine Multilayers Quantitated by Ellipsometry," *J. Biol. Chem.*, 258(4):2426–2431 (1983).

Giesen et al., "Membrane–mediated Assembly of the Prothrombinase Complex," *J. Biol. Chem.*, 266(28):18720–18725 (1991).

Giesen et al., "Production of thrombin as a probe for mixing of phospholipids in membranes on solid supports," *Biochimica et Biophysica Acta*, 1237:43–48 (1995).

Frederik and Mosbach, "Detection of Biospecific Interactions Using Amplified Ellipsometry," *Analytical Biochemistry*, 170:68–72 (1988).

Nygren, "Experimental demonstration of lateral cohesion in a layer of adsorbed protein and in layers of gold–antibody complexes bound surface immobilised antigen," *J. Immun. Meth.*, 114:107–114 (1988).

Reeves et al., "Liposome immunosensing devices for environment contaminant screening," *Trends in Analytical Chemistry*, 14(7):351–355 (1995).

Rongen et al., "Development of a liposome immunosorbent assay for human interferon–γ," *Analytica Chimica Acta*, 287:191–199 (1994).

Wilems et al., "Adsorption and Conversion of Prothrombin on a Rotating Disc," *Blood*, 82(2):497–507 (1993).

* cited by examiner

*Primary Examiner*—Long V. Le
*Assistant Examiner*—Kartic Padmanabhan
(74) *Attorney, Agent, or Firm*—Banner & Witcoff, Ltd.

(57) ABSTRACT

An immunoassay, e.g. ELISA, method and kit for determining (preferably quantitatively) an analyte adsorbed at a surface or present in a liquid sample, comprising binding the analyte to a solid phase, attaching a marker to the analyte, and detecting marker attached to the solid-phase. The invention proposes to use a combination of marker and detection (e.g. an enzyme-substrate combination) which is capable of producing a precipitate on a solid phase which carries the marker and to detect the binding of analyte to the solid phase by in-situ determining the change in surface mass of the solid phase due to the formation of the precipitate. Ellipsometry is an example of a technique suitable for determining the change of surface mass of the solid phase, which could be made of a silicon- or chromium-sputtered glass slide. The invention shortens the assay time and/or improves the assay sensitivity, and allows to measure extremely low surface concentrations of analytes of interest.

18 Claims, 1 Drawing Sheet

IMMUNOASSAY METHOD AND KIT

Figure 1:
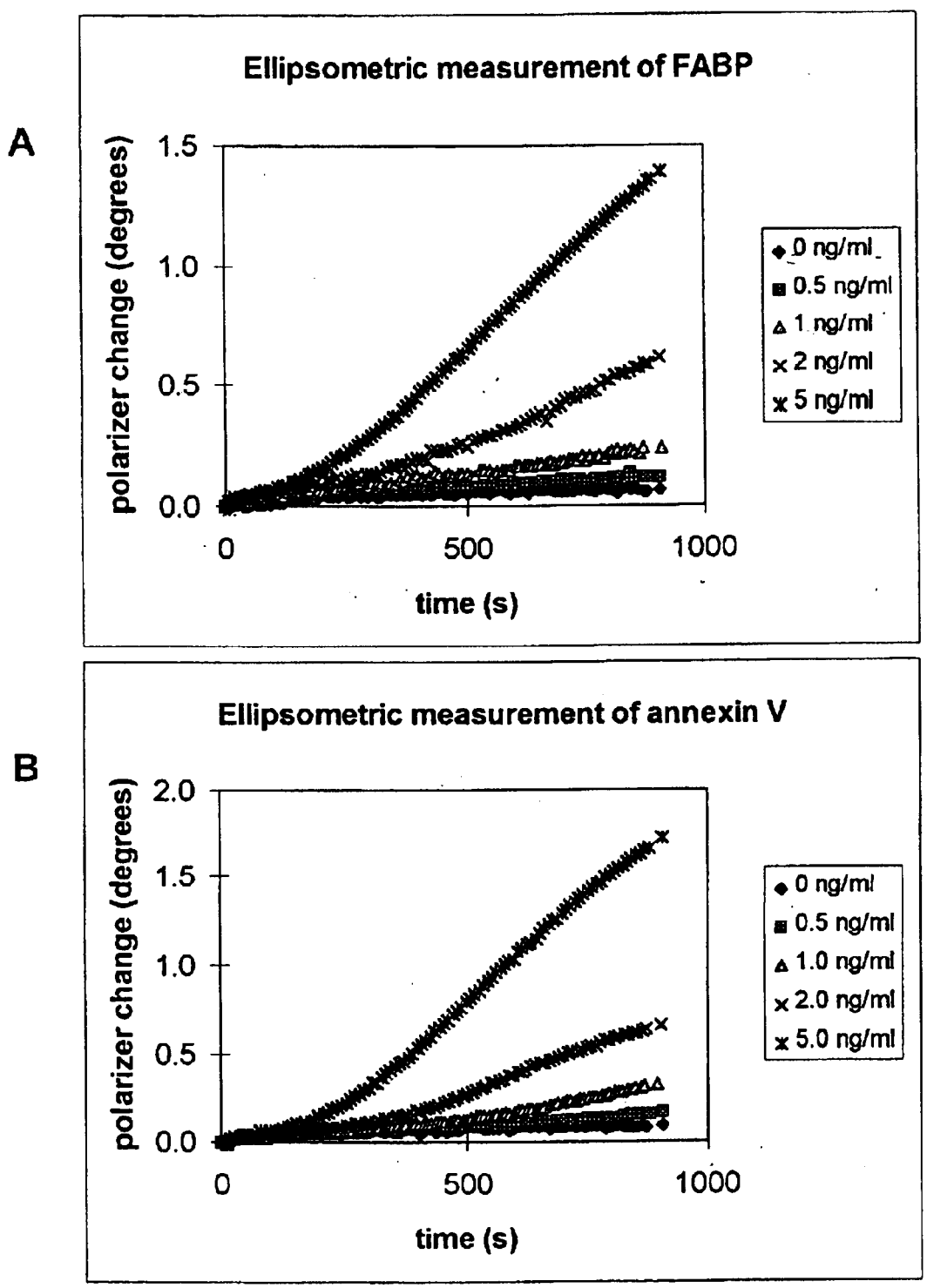

This is a continuation application of international application No. PCT/NL98/00670, filed Nov. 25, 1998; which claims priority from European patent application no. 97203758.4, filed Dec. 1, 1997.

FIELD OF THE INVENTION

The subject invention is in the field of immunoassays for determining, an analyte, especially an analyte adsorbed at a surface, or analyte as it occurs in a liquid sample in solution or at a particular location therein, such as at a specific surface.

More in particular, the invention relates to enzymelinked immunosorbance assays (ELISA's) for determining the concentration of an analyte in a liquid sample, including its concentration in the bulk of the liquid sample or its concentration at a particular surface. Specifically, the present invention relates to new immunoassay methods and kits specifically adapted for carrying out these new immunoassay methods.

BACKGROUND OF THE INVENTION

Immunoassays, such as ELISA's, are widely used for the determination, either qualitative or, mostly, quantitative, of a nearly unlimited variety of organic substances, either of natural origin or synthetic chemical compounds, such as peptides, proteins, enzymes, hormones, vitamins, drugs, carbohydrates, etc., for various purposes, such as in particular for diagnostic purposes, but also for forensic applications, food quality control, and generally for any analytic purpose. All such substances to be assayed will be referred to herein generally as analytes.

Many different variants of ELISA methods exist. The description given hereunder aims at illustrating a typical ELISA technique. It does not pretend to be complete and should not be construed in any way as restricting the scope of the present invention. For example, in the following description, ELISA methods are described as comprising separate steps of incubating a sample with a first binding partner of the analyte and incubating the reaction product formed with a second binding partner of the analyte (herein binding partners of the analyte will sometimes be referred to as binding partners for the analyte). However, some existing ELISA embodiments do not comprise such separate incubation steps and allow the analyte to react simultaneously, or shortly one after the other, in one and the same incubation step, with both its first and second binding partners. Competitive ELISA's are another example of ELISA variants not discussed in detail herein. The subject invention is in principle applicable to any and all ELISA variants, and to similar immunoassay methods which, strictly speaking, are not ELISA methods, e.g. because they do not involve the use of an enzyme.

In a typical ELISA, to detect the presence, or measure the concentration, of an analyte of interest, especially in a liquid sample, which may be a body fluid such as blood, plasma, serum, urine, saliva, sputum, etc., the sample is contacted with a first binding partner for the analyte, and the sample and the binding partner for the analyte are incubated for a sufficient time to allow analyte contained in the sample to bind to the binding partner.

A typical example of such a binding partner is an analyte-specific antibody, e.g. a monoclonal antibody with specificity for the analyte in question. However, other kinds of substances and structures may also qualify as a binding partner. For example, the natural receptor of the analyte in question could be useful as a binding partner, as well as other substances and structures to which the analyte can bind. The binding partner would normally be a specific binding partner, but this is not a requirement. It is even possible to work without a first binding partner and to immobilize (i.e. bind to a solid phase) the analyte either directly (e.g. by adsorption) or through a non-specifically binding linker substance. All of such variants are explicitly intended to be included in the scope of this invention. The words "analyte adsorbed at a surface" as used herein refer to any method resulting in attachment or binding of analyte to a surface.

Usually, said first binding partner is used in an immobilized form, i.e. attached to a solid phase, such as polystyrene beads or the inner surface of the reaction container (e.g. a reaction tube or a well of a microtiter plate). The binding partner may be physically adsorbed onto the solid phase or, usually, be attached by covalent binding. According to some ELISA embodiments, the binding partner is attached by using a suitable coupling agent, and in others by using appropriate linker substances, such as biotin and (strept) avidin. In some ELISA embodiments, the immobilization of the binding partner is carried out after the incubation of the sample and binding partner, thereby allowing the reaction between analyte and binding partner to proceed in the liquid phase. To allow its subsequent immobilization, said binding partner may be applied in a biotinylated form. Immobilization can then be effected by using a solid phase carrying (strept)avidin.

As a result of this first reaction, any analyte present in the sample will have become bound to its binding partner and thereby to the solid phase. Usually after the liquid has been removed and the solid phase has been washed, steps are taken to make the result detectable. The solid phase having attached thereto the binding partner and analyte, if any, is contacted with a second binding partner for the analyte. Again, a specific binding partner is the rule, but not strictly required. Usually, this second binding partner carries a label/marker allowing its detection. In some ELISA embodiments, however, the second binding partner is used in unlabelled form and is labelled after its binding by using a labelled binding partner for the second binding partner. As an example thereof, the second binding partner may be a mouse antibody (either polyclonal or monoclonal) against the analyte in question, and after its binding to the analyte which had been attached via its first binding partner to the solid phase, a labelled goat anti-mouse IgG is used to attach a label to the immobilized complex.

In ELISA'S, the label consists of an enzyme capable of a detectable conversion of a substrate, e.g. a peroxidase such as horseradish peroxidase, capable of converting, in the presence of hydrogen peroxide, a substrate, such as 3,3'5, 5'-tetramethylbenzidine, into a coloured product.

Normally, after the enzyme-labelled reactant has been attached to the immobilized complex, the solid phase with complex bound thereto is washed before the actual detection phase is entered.

In the detection phase, substrate solution is added to the solid phase with attached complex and the conversion, if any, of the substrate is detected. To allow quantitative measurement of the analyte, the solid phase is incubated with the substrate solution for a fixed time, which should be sufficiently long to allow a substantial enzymatic conversion of the substrate into a coloured substance. After termination of the substrate-converting reaction the intensity of the colouration, which is proportional to the immobilized amount of enzyme, is measured by optical means, such as a photometer to measure the absorbance at a chosen wavelength, such as 450 nm.

A disadvantage of the existing ELISA techniques is that the adsorption and detection phases, to secure assay sensitivity, are very time consuming for low analyte concentrations. The rate of adsorption of analyte to the surface is proportional to the concentration of analyte in the solution, and thus will also become very low, even in well-stirred systems. To allow a reliable measurement of analytes present in a liquid at a concentration in the order of nanograms or even picograms per ml, the adsorption phase may require a reaction time of one to several hours.

Another disadvantage of the existing ELISA techniques is that they do not allow to measure extremely low surface concentrations of analytes, such as occur at the surface of biological (model) membranes.

An object of this invention is to provide a modified immunoassay, e.g. ELISA, technique allowing to reduce the incubation time in the adsorption and/or detection phase, or to increase the sensitivity of the assay, or both.

A further object of this invention is to provide a modified immunoassay, e.g. ELISA, technique which allows to measure analyte concentrations at a particular surface.

Another object of this invention is to provide products specifically adapted for carrying out such modified immunoassay techniques.

The invention pertains to a fundamental modification of the assay principle of immunoassays, e.g. ELISA's, in which the measurement of the accumulation of enzyme product in the (bulk phase) solution is replaced by in-situ measurement of the accumulation of precipitate on a solid surface. The subject invention involves the use of a precipitate forming system, such as an enzyme-substrate combination which leads to the formation of a precipitate on a solid surface, and measurement of the surface mass, e.g. by ellipsometry or other surface mass measurement techniques.

By using this invention, very low concentrations of adsorbed analyte on the solid surface can be determined and the adsorption phase of analyte from the liquid to the surface can be substantially shortened. Also, the time-consuming build up of product concentration in the bulk liquid phase is no longer required, and is replaced by an adsorption of a thin layer of precipitate, of only molecular dimensions, on the solid surface. This modification implies a large increase in assay sensitivity and offers the possibility of much shorter assay times. It also allows to determine extremely low surface concentrations as may occur at the surface of biological (model) membranes.

Determination of analyte concentrations by 'immunoprecipitation' is a well known technique. The precipitate of analyte-antibody aggregates, formed by this method after addition of the precipitating antibody, is usually simply allowed to sediment, collected and weighed. In spite-of poor precipitation when either the analyte or the antibody is present in large excess, it has been shown that under well defined conditions this technique allows quantitative interpretation of data (see e.g. European patent application 0 368 462). In a more sensitive and rapid version of this technique, (latex) particles coated with antibody are added and aggregate formation is measured by light scattering. In this way, the time-consuming sedimentation is avoided and measurements may be completed in seconds. The present method is fundamentally different from these techniques. In said techniques the analyte is not concentrated at a solid/liquid interface and the amount of precipitate is not continually increasing in time, as when it is produced by an enzyme. Due to these factors, and due to a specific aggregation, such techniques have a limited sensitivity and generally do not allow measurement of analyte concentrations below the ng/ml range.

Analytical methods which involve an enzyme-directed formation of a (coloured) precipitate are known per se. Such a method is known for example in the field of immunocytochemistry. In this known method, to demonstrate the presence and/or localization of various tissue proteins in histological studies, a specific protein in the tissue is determined by first producing thin tissue sections, after freezing the tissue or using various forms of chemical fixation, and then adding antibodies which specifically recognize and bind to the protein. Excess antibodies are removed and then a second, enzyme-linked, antibody, for instance an IgG-HRP conjugate, is added. After removal of excess conjugate, a suitable substrate, such as 3,3'-diaminobenzidine (DAB), is added. If the specific protein is present in the tissue, a localized staining due to the formation of a DAB-derived precipitate will occur.

The present invention, however, does not relate to the localization and detection of proteins in tissue but to the detection and measurement of analyte (concentrations) adsorbed at solid surfaces or present in solutions. Furthermore, the subject invention applies a (preferably quantitative) measurement of surface mass (in the $ng/cm^2$ range) whereas, in said known immunocytochemical method, qualitative results are obtained, usually by visual or microscopic inspection. In some studies, the intensity of staining has been measured by applying optical density measurements, but the technique has never been combined with a technique for quantitative measurement of surface mass, such as ellipsometry or others. This would also be very difficult to perform because the thickness of tissue sections (micrometers) is of another order of magnitude than the thickness of the precipitate layers (nanometers) measured in the method of the present invention.

The prior art suggests to use immunoassays based on optical interference on specially prepared optically active receptive surfaces, coated by thin oxide-, nitride or polymer films. Using such pre-coating, the additional adsorption of a precipitate layer results in visually detectable colour changes. Such applications have been presented in the U.S. Pat. No. 5,418,136. Apart from visual detection of precipitate formation, measurement of the precipitate by ellipsometry was also applied. However, the various rinsing and/or drying steps required in these techniques preclude the high sensitivity that can be obtained by in-situ measurement. For the detection of very low analyte concentrations in. biological fluids like plasma, serum, blood, milk or urine, the a specifically adsorbed mass of other bulk substances, such as albumin, will often exceed the minute amounts of adsorbed precipitate, and rinsing or drying will cause changes in surface mass far surpassing the specific effect. In-situ measurement also offers the possibility of a one-step ELISA, in which the analyte, the conjugate and the chromogenic substrate are added together, without intervening washing or drying steps. In a normal ELISA this would be impossible, because the colour production by the excess of unbound conjugate would far surpass the colour production of the small amount of analyte-bound conjugate on the surface. In contrast, the presented technique only measures the precipitate produced by surface-bound conjugate. In addition to a higher sensitivity, the present use of in-situ measurement also allows a more rapid assay, because time-consuming rinsing and/or drying steps, with subsequent separate measurement of the precipitate, are avoided.

Another fundamental difference with the techniques described in the two mentioned patents is that no specially prepared optically active or polymer-coated surfaces are required according to the present invention. Such surfaces are expensive, just like the optically active slides used in techniques based on surface plasmon resonance (SPR), whereas cheap (disposable) reflecting surfaces, such as silicon wavers or chromium-sputtered glass slides, can be used in the present method.

The prior art suggests to use amplified ellipsometry as a means of enhancing the sensitivity of protein adsorption measurements [5]. In the prior art method concerned, the mass of the tagging antibody was increased by coupling it to silica particles. Antibody-coated gold particles have also been used, mainly combined with electron microscopy in localization studies [6]. Another prior art technique for amplification of surface mass uses biotinylated or analyte-coated liposomes [7,8].

These techniques are fundamentally different from the subject invention because they do not measure a continuing accumulation of precipitate per tagging molecule, but simply use heavier tags. Because of their slower diffusion towards the surface, the advantage of better detectability of such heavy tags has to be balanced against their slower adsorption, and this hampers the use of these methods for rapid assays.

SUMMARY OF THE INVENTION

The invention provides an immunoassay method for determining an analyte adsorbed at a surface or present in a liquid sample, comprising binding said analyte to a solid phase, attaching a marker to the analyte, and detecting marker attached to said solid-phase, wherein a combination of marker and detection means is used which is capable of producing a precipitate on a solid phase which carries the marker and binding of analyte to the solid phase is detected by in-situ determining surface mass of said solid phase due to formation of said precipitate.

Furthermore, the invention provides a kit for carrying out an immunoassay method for determining an analyte adsorbed at a surface or present in a liquid sample, wherein the kit comprises at least one means specifically adapted for carrying out the method according to the present invention.

BRIEF DESCRIPTION OF THE BRAWINGS

The FIGURE shows the results of a precipitate-enhanced ellipsometric measurement of fatty acid-binding protein (a) and annexin V (b) on PVC-coated silicon discs.

DETAILED DESCRIPTION OF THE INVENTION

The present invention provides, in a first aspect, an immunoassay method for determining an analyte adsorbed at a surface or present in a liquid sample, comprising binding said analyte to a solid phase, attaching a marker to the analyte, and detecting marker attached to said solid-phase, wherein a combination of marker and detection means is used which is capable of producing a precipitate on a solid phase which carries the marker and binding of analyte to the solid phase is detected in-situ by determining the surface mass of said solid phase due to formation of said precipitate.

The term 'in-situ detection' is intended to reflect that a change in surface mass is determined as the precipitate is formed. In other words, no flushing, drying, rinsing, or other manipulations are carried out, which might lead to errors in the measured result due to their effecting an additional change in surface mass. Moreover, the in-situ detection advantageously allows measurement of precipitate formation by surface-bound enzyme, even in the presence of substrate conversion by excess enzyme in the solution phase (one-step ELISA).

As indicated above in the background section, the invention pertains to a great variety of different immunoassay methods. Most have in common that the analyte, if present in the sample, is bound to the solid phase through the intermediary of a binding partner of the analyte, usually a specific binding partner, such as an antibody which specifically binds said analyte. However, in some embodiments the analyte may be bound to the solid phase directly, by adsorption, or by non-specific linking means.

Said binding partner, if used, may have been attached to the solid phase in advance. Alternatively, it is bound to the solid phase after having reacted with the analyte, if present.

Most immunoassay embodiments will furthermore have in common that a second binding partner of the analyte is used to attach a marker to the analyte. Again, the binding partner, if used, will preferably be a specific binding partner, such as an antibody specifically binding to the analyte.

This second binding partner of the analyte may carry the marker. Alternatively, however, the marker is carried by a substance capable of binding to said second binding partner of the analyte. For example, if said second binding partner of the analyte is a murine monoclonal antibody against the analyte, the marker may be attached directly to this monoclonal antibody, or alternatively be attached to an anti-mouse Ig antibody (i.e. an antibody specifically binding to murine immunoglobulines).

The attachment of the marker to the analyte can either be carried out simultaneously with the attachment of the analyte to the solid phase, or before it, or after it. In most inmunoassay methods, it is preferred to first immobilise the analyte and only subsequently bind the marker to the immobilised analyte.

Preferably, the method is a quantitative method to determine the concentration of the analyte in the sample. In another preferred embodiment, the subject method is a quantitative method to determine the concentration of the analyte at a particular surface. The surface in question can be a biological (model) membrane, i.e. the surface of a cellular membrane, or an artificial surface, e.g. an artificial surface intended to mimic a naturally occurring surface of interest, preferably deposited on a uniform accessible surface and allowing quantitative interpretation of precipitate formation. The invention is not restricted to quantitative methods, however, and may be useful to qualitatively determine the presence of an extremely low concentration of analyte in the sample, either in the bulk of the sample or at a particular location, such at a particular surface.

Preferably, the change of surface mass of the solid phase is determined by ellipsometry. However, the invention extends to other techniques for determining the change of surface mass of the solid phase, such as surface plasmon resonance and total internal reflection fluorescence.

In the most preferred embodiments of the invention, said marker is an enzyme and said detection means comprise a substrate of said enzyme. Preferably, the immunoassay is an ELISA method. Preferably, a horseradish peroxidase is used as the enzyme and 3,3'-diaminobenzidine as the substrate. However, the subject invention extends to other enzyme-substrate combinations capable of producing a precipitate, such as an alkaline phosphatase as the enzyme and 5-bromo-4-chloro-3-indolylphosphate and nitroblue tetrazolium as substrate. Further, the invention covers any other combination of marker and detection means that is capable of producing a precipitate on a solid phase which carries said marker. For example, formation of a precipitate may be the result of nucleation, by nucleated growth of metal, or non-metal particles, or the result of chain or polymerisation reactions, of, e.g. unsaturated hydrocarbons which can be polymerised by exposure to ultraviolet radiation, etc. So, said marker could comprise an unsaturated hydrocarbon and said detection means a further amount of the same or a different hydrocarbon together with means to initiate polymerisation (such as UV radiation). Alternatively, said marker could comprise colloidal particles of a metal, e.g. gold, silver, etc., or a non-metal, e.g. selenium, tellurium, carbon, silica, etc., while said detection means comprise a source of a further amount of the same or a different metal or non-metal, together with means (e.g. a suitable reducing agent, such as a borohydride compound, capable of liberating the metal from a chemical compound containing said metal) to promote growth of the colloidal particles used as the marker.

According to the present invention, it is preferred that a silicon slide is used as the solid phase. However, the invention extends to other solid phases suitable for use in a technique to determine the change of surface mass of the solid phase, such as a chromium-sputtered glass slide. In principle the solid phase may consist of any simple and cheap reflecting surface and does not require pre-treatment like deposition of special optically active layers, as described in U.S. Pat. No. 5,418,136.

The amount of analyte adsorbing to solid surfaces will generally be dependent on the transport conditions (diffusion and stirring) in the system. In the usual laminar flow systems this implies that adsorbed amounts may decrease in the downstream direction, because the fluid boundary layer becomes progressively depleted of analyte. This site-dependency of the amount of adsorbed analyte may hamper quantitative description of the rate of precipitate formation, for instance, if first the biological effect of a minute quantity of protein adsorbed on a membrane is measured [4] and then the amount of protein responsible for this effect would be measure. It has been found that this problem may be overcome by performing the present method quantitatively on so-called uniform-accessible surfaces, that is, with identical adsorption conditions over the whole surface. Using such a surface, the biological effect can be related to the adsorbed amount of analyte, expressed per unit surface area. A uniform-accessible surface, a rotating disc in solution, has been developed and allows ellipsometric measurement of analyte adsorption on its surface [9]. Combination with ellipsometry on a rotating disc is therefore a preferred embodiment of the present invention.

Furthermore, in a second aspect, the present invention provides a kit for carrying out an immunoassay method for determining an analyte in a liquid sample, wherein the kit comprises at least one means specifically adapted for carrying out the method according to the present invention.

In particular, said means comprise a solid phase suitable for the application of a technique for determining the change of surface mass of the solid phase, such as a silicon or chromium-sputtered glass slide. Preferably, said solid phase carries a binding partner for the analyte, most preferably a specific binding partner.

The kit could furthermore contain various conventional constituents, with the proviso that it comprises a marker and detection means which, in combination, are capable of producing a precipitate, most preferably an enzyme and a substrate which, in combination, are capable of producing a precipitate.

The adsorption of analytes from buffer solutions onto, and more generally the accumulation of solid substances on planar surfaces may be detected and quantified by means of ellipsometry. This is an optical technique using reflection of monochromatic light against the adsorbing surface, which technique allows a quantitative measurement of analyte adsorption with a detection limit of 1–5 ng/cm$^2$.

The reflecting surface, in the examples given herein a pre-treated silicon slide, is placed, for instance, in a quartz cuvette filled with, e.g., 5 ml of buffer solution. Monochromatic light from a He—Ne laser, with a wavelength of 632.8 nm, first passes through a polarizing prism P and then through a quarter-wave plate with its fast axis at 45 degrees to the plane of incidence. The light then enters the cuvette, is reflected against the silicon slide, exits the cuvette, passes through a second polarizing prism A, and is finally detected by a photodiode. The positions of P and A are computer-adjusted such as to keep the resulting light intensity reaching the photodiode at a minimum. When a solid substance adsorbs to the reflecting surface, the positions of P and A are changed in order to keep the intensity minimal. Such adsorption will thus cause a change in the positions of the 'polarizer' P and the 'analyzer' A. In the special case of silicon slides as reflecting surface and organic substances, such as proteins, lipids, sugars or organic precipitates as adsorbing analytes, the change in adsorbed surface mass is directly proportional to the change in the polarizer. The slides used in the examples were cut from silicon wafers (Wacker Chemitronic; n-type, phosphorus-doped). Measurements were performed at room temperature (20° C. ±1° C.) under continuous stirring by a rotating stir. The instrument and analysis of data have been described in earlier publications of our group [1,2].

In a typical experiment, the pre-treated slide is placed in the ellipsometer cuvette and a null-reading is performed (P0,A0). Then the protein to be assayed is added to the buffer and allowed to adsorb onto the slide for a suitable time, for example 5 minutes. For very low protein concentrations, as used in the present report, the amount of protein adsorbing in this period of time remains below the ellipsometer-detection limit, so the positions P0 and A0 remain essentially unchanged. The cuvette is then flushed with fresh buffer and the free surface space on the slide is blocked by adsorption of albumin or other bulk proteins. An Antibody-horseradish peroxydase (HRP) conjugate is then added and allowed to adsorb for a suitable time, for example two minutes. Again the cuvette is flushed, and a substrate solution containing 3,3'-diaminobenzidine (DAB) and $H_2O_2$ is added. On sites where conjugate molecules have bound to the adsorbed protein, DAB-precipitate will be formed by the enzymatic action of HRP. Because of the continuing DAB conversion, the surface mass of precipitate will soon be much larger than the original protein mass and will become detectable by ellipsometry.

In another set-up, aiming at determination of very low protein concentrations, the flushing steps between addition of analyte, conjugate and precipitaxing substrate are discarded and the analyte, conjugate and DAB-substrate is added together or shortly after each other. In this way, a one-step ELISA is obtained.

According to the invention, the measurement of the rate of precipitate formation on the solid surface is preferably performed by ellipsometry. However, the assay principle of the present invention could equally well be applied to other techniques for quantitative measurement of surface mass, such as other forms of reflectometry than ellipsometry, surface plasmon resonance (SPR) and total internal reflection fluorescence (TIRF). Ellipsometry is a special form of reflectometry and simpler forms of it do exist, for instance embodiments omitting the quarter-wave plate. These techniques have as a common feature that light reflection occurs at the same side of the reflecting surface as analyte adsorption. For SPR and TIRF this is not true and light reflection occurs at the non-adsorbina side of the slide.

In SPR, a so-called 'evanescent' light wave, emerging at the other side of the slide, is sensitive to the refractive index of the adsorbed analyte layer. At a certain angle of incidence, an optical resonance occurs, and the adsorbed mass of analyte can be calculated from these data. SPR has approximately the same detection limit as ellipsometry, but the reflecting slides need a thin layer of a substance with a high refraction index on the analyte-adsorbing side of the slide, usually a thin gold layer. Because this layer has to satisfy narrow specifications, SPR slides are expensive. In contrast, the silicon slides used in an ellipsometer are cheap and can be used as disposables.

For TIRF, the evanescent wave occurs at an angle of incidence leading to total reflection. The wave penetrates a short distance into the solution and excites fluorescent probes attached to the analytes. The intensity of the fluorescent signal is proportional to the adsorbed amount of analyte. No expensive slides are required, but the technique is less sensitive than ellipsometry or SPR.

Apart from different techniques for measurement of surface mass, different enzyme-substrate combinations could also be used in the present invention as long as they would produce a precipitate. Instead of the exemplified system of horseradish peroxydase (HRP) and 3,3'-diaminobenzidine (DAB), for instance, alkaline phosphatase (AP) could be used as the enzyme and 5-bromo-4-chloro-3-indolylphosphate (BCIP) with nitroblue tetrazolium (NBT) as substrates. Any other enzyme/substrate combination, or even precipitate formation not based on enzymatic conversion but, for instance, on nucleation, could also be used.

In addition, although the examples given herein illustrate the determination of protein concentrations in buffer solutions, the principle is also valid for any other type of solution or suspension, notably the ones which are used for medical purposes such as urine, plasma or whole blood.

To illustrate the invention, the examples given herein relate to three different protein assays, differing with respect to the protein (analyte) to be assayed, but also differing with respect to surface preparation and detection principle.

Example 1 concerns an assay of annexin V. Annexin V is an intracellular protein with a still unknown biological function. Annexin V has been used as a model protein because of the well-defined parameters for its adsorption on phospholipid membranes. It is a protein which, in the presence of calcium, has high binding affinity for phospholipid membranes, provided that these membranes contain aminophospholipids such as phosphatidylserine (PS). The adsorption process is transport-limited, and the rate of annexin V adsorption can be accurately calculated from the stirring conditions and the annexin V concentration in solution. As shown in example 1, annexin V was directly adsorbed onto silicon slides, which had been pre-coated with phospholipid bilayers, and detected with a two-step immunoprocedure according to the invention. Said phospholipid bilayers are an example of a specific binding partner which is not an antibody to the analyte in question. This example shows that binding of annexin V to membranes can be studied with the present invention in the normal physiological concentration range of annexin V in plasma of 1–5 ng/ml.

In example 2, fatty acid-binding protein (FABP) (and also annexin V) were determined on polyvinylchloride (PVC) coated silicon slides, using the sandwich-principle for detection. FABP is a cardiac marker protein with a normal plasma concentration of 1–2 ng/ml, which is presently under investigation as an early marker for acute myocardial infarction, and as a marker for successful reperfusion therapy after acute myocardial infarction. Present day ELISA's for this protein take about one hour of assay time, while this time could be reduced to a few minutes with the technique of the subject invention. Using a dedicated instrument, this would allow rapid bedside measurement.

Example 3 illustrates use of the invention for assaying interleukine 6 (IL6). IL6 is an important mediator of the inflammatory response, with a normal plasma concentration below 10 pg/ml. Determination of such concentrations with conventional ELISA's presently takes several hours, while it can be performed, as demonstrated herein, within 30 minutes using the newtechnique of the invention. For IL6, the catcher antibody was adsorbed for only 15 minutes on strongly hydrophobic (silanized) silicon slides, and the biotin-streptavidin system was used for detection.

These examples demonstrate that the method can be used for a broad range of surfaces and detection principles. Other reflecting surfaces than silicon slides, for instance chromium-sputtered glass slides, could equally well be used and have in fact been used by our group in the past [1,2].

Considering these circumstances, the following aspects are considered part of the invention:
1) Quantitative measurement of the concentrations of. specific analytes, such as proteins, peptides, sugars, etc, in solutions, by means of in-situ ellipsometric measurement of (the rate of) accumulation of precipitate formed by the continuous action of (enzyme)-molecules that either bind directly to the surface-bound analyte or are coupled to other molecules that bind to these analytes.
2) The use of principle 1) for the measurement of the concentrations of such analytes in any type of solution or suspension, such as distilled water, buffer solutions, physiological saline, urine, plasma, whole blood etc.
3) The use of principle 1) combined with other techniques for quantitative measurement of surface mass, such as other forms of reflectometry than ellipsometry, surface plasmon resonance, total internal reflection fluorescence etc.
4) The use of principle 1) combined with any other form of reflecting surfaces or other forms of surface preparation, such as pre-coating of reflecting surfaces with phospholipids or polymers.
5) The use of principle 1) combined with any modification of detection principle, such as other enzyme/substrate combinations or precipitate-forming reactions, sandwich techniques, single versus multiple enzyme molecule tags, direct or competitive binding etc.
6) The use of principle 1) in an immunoassay with simultaneous addition, or addition shortly after each other, of analyte, conjugate and precipitate-forming substrate, without intervening rinsing or flushing steps (one-step ELISA).
7) Combination of principle 1) with the use of a uniformly-accessible surfaces, preferably a rotating disc, for quantitative description of the rate of precipitate formation and for the expression of surface-bound (biological) activity in the amount of bound active agent per unit surface area.

EXAMPLE 1

Determination of Annexin V Concentrations

Silicon slides were covered with phospholipid bilayers by addition of 20 μM phospholipid vesicles, obtained by sonication of a 20% DOPS/80% DOPC mixture, as described [3,4]. After formation of a stable phospholipid bilayer on the surface, excess phospholipid was removed by flushing the cuvette with buffer, and human annexin V was added. After 200 s of adsorption, the cuvette was flushed and rabbit polyclonal anti-annexin V was added for 120 s. The cuvette was flushed again and a swine anti-rabbit IgG, conjugated to HRP, was added for 120 s. Again the cuvette was flushed, 0.278 mM DAB and 0.834 mM $H_2O_2$ was added and the formation of precipitate on the surface was measured by ellipsometry. Results are shown in Table 1.

TABLE 1

Determination of annexin V concentrations.

| buffer conc. of annexin V | calculated surface mass of annexin V | incubation time in DAB | | |
|---|---|---|---|---|
| (ng/mL) | (ng/cm2) | 300 s | 600 s | 900 s |
| 0.00 | 0.00 | 0.037 ± 0.005 | 0.046 ± 0.004 | 0.060 ± 0.006 |
| 0.036 | 0.01 | 0.056 ± 0.007 | 0.075 ± 0.009 | 0.115 ± 0.008 |
| 0.18 | 0.05 | 0.063 ± 0.007 | 0.118 ± 0.013 | 0.192 ± 0.017 |
| 0.36 | 0.10 | 0.102 ± 0.008 | 0.236 ± 0.018 | 0.388 ± 0.023 |
| 0.90 | 0.25 | 0.258 ± 0.021 | 0.689 ± 0.058 | 1.136 ± 0.097 |
| 1.80 | 0.50 | 0.765 ± 0.070 | 1.843 ± 0.109 | 2.953 ± 0.140 |

Values indicate polarizer changes in degrees (±SD) of four experiments.

If the detection limit is defined as a polarizer change exceeding the polarizer change plus 3 times the SD for the blank, it follows from Table 1 that the lowest surface concentration of 0.01 ng/cm$^2$, which is about 100 times lower than detectable by direct ellipsometry, could already be measured within 300 s incubation time.

EXAMPLE 2

Determination of FABP Concentrations

Silicon slides were coated with homogeneous PVC layers of 20–25 nm thickness by an automated dipping procedure of the slides in a solution of PVC in cyclohexanone. The slides were coated with monoclonal antibodies against FABP (and annexin V) by overnight adsorption, and free surface space was blocked with either albumin or skimmed milk powder. The slides were then exposed for 10 min to various concentrations of FABP (or annexin V), and the adsorbed proteins were detected directly with monoclonal antibody/HRP conjugates or, for annexin V, with the described two step procedure. Precipitate formation after addition of DAB, as measured by ellipsometry, is shown in the Figure. A concentration of 0.5 ng/mL could be measured within 120 s of DAB conversion time.

EXAMPLE 3

Determination of IL6 Concentrations

A monoclonal catcher antibody against IL6 was adsorbed for only 15 minutes on strongly hydrophobic (silanized) silicon slides, and various concentrations of IL6 were added for only 10 min. Two short incubation steps with biotinylated anti-IL6 antibodies and streptavidin-labeled (multi) HRP followed. Results of ellipsometric measurement of precipitate formation after addition of DAB are shown in Table 2. A concentration of 10 pg/mL IL6 could be measured in less than 300 s DAB conversion time and a total assay time of less than 30 min.

TABLE 2

Determination of IL6 concentrations.

| IL6 concentration (pg/mL) | number of experiments | incubation time in DAB | | |
|---|---|---|---|---|
| | | 300 s | 600 s | 900 s |
| 0 | 3 | 0.07 ± 0.03 | 0.08 ± 0.03 | 0.08 ± 0.03 |
| 10 | 6 | 0.29 ± 0.07 | 0.44 ± 0.10 | 0.50 ± 0.10 |
| 100 | 3 | 9.4 ± 0.7 | 11.7 ± 0.7 | 12.9 ± 0.9 |

Values indicate polariser changes in degrees (±SD).

References

1. Cuypers P A, Corsel J W, Janssen M P, Kop J M M, Hermens W Th, Hemker H C. The adsorption of prothrombin to phosphatidylserine multilayers, quantitated by ellipsometry. J Biol Chem 1983; 258: 2426–31.
2. Corsel J W, Willems G M, Kop J M M, Cuypers P A, Hermens W Th. The role of intrinsic binding rate and transport rate in the adsorption of prothrombin, albumin and fibrinogen to phospholipid bilayers. J Colloid Interface Sci 1986; 111: 544–54.
3. Giesen P L A, Willems G M, Hemker H C, Hermens W Th: Membrane-mediated assembly of the prothrombinase complex. J Biol Chem 1991; 266: 18720–5.
4. Giesen P L A, Hemker H C, Hermens W Th: Production of thrombin as a probe for mixing of phospholipids in membranes on solid supports. Biochim Biophys Acta 1995; 1237: 43–8.
5. Mandenius C F, Mosbach K. Detection of biospecific interactions using amplified ellipsometry. Anal Biochem 1988; 170: 68–72.
6. Nygren H. Experimental demonstration of lateral cohesion in a layer of adsorbed protein and in layers of gold-antibody complexes bound to surface-immobilized, antigen. J Immunol Meth 1988; 114: 107–114.
7. Rongen H A H, van der Horst H M, Hugenholtz G W K, Bult A, van Bennekom W P. Development of a liposome immunosorbent assay for human interf6ron-gamma. Anal Chim Acta 1994; 287: 191–199.
8. Reeves S G, Siebert S T A, Roberts M A, Durst R A. Liposome immunosensing devices for environmental Contaminant screening. Trends in Anal Chem 1995; 14: 351–355.
9. Willems G M, Giesen P L A, Hermens W Th: Adsorption and conversion of prothrombin on a rotating disc. Blood 1993; 82: 497–504.

What is claimed is:

1. An immunoassay method comprising:
   (a) binding an analyte to a solid phase,
   (b) attaching a marker to the analyte,
   (c) allowing the marker to produce a precipitate, and
   (d) detecting said precipitate as it is formed on the solid phase without intervening steps by determination of a change in surface mass of said solid phase due to formation of said precipitate.

2. The immunoassay method according to claim 1, wherein step (d) quantitatively determines the concentration of analyte in a sample.

3. The immunoassay method according to claim 1, wherein step (d) includes measuring surface concentrations of analyte adsorbed or bound on the solid phase.

4. The immunoassay method according to claim 1, wherein the change in surface mass of the solid phase is determined by ellipsometry.

5. The immunoassay method according to claim 4, wherein the ellipsometry is carried out on a uniform-accessible surface.

6. The immunoassay method according to claim 1, wherein the change in surface mass of the solid phase is determined by surface plasmon resonance.

7. The immunoassay method according to claim 1, wherein the change in surface mass of the solid phase is determined by total internal reflection fluorescence.

8. The immunoassay method according to claim 1, wherein said marker is an enzyme and the enzyme binds to a substrate of said enzyme.

9. The immunoassay method according to claim 8, wherein the enzyme is a horseradish peroxidase and the substrate is 3,3'diaminobenzidine.

10. The immunoassay method according to claim 8, wherein the enzyme is an alkaline phosphatase and the substrate is 5-bromo-4-chloro-3-indolylphosphate and nitroblue tetrazolium.

11. The immunoassay method according to claim 1, performed as a one-step ELISA.

12. The immunoassay method according to claim 1, wherein the solid phase is silicon.

13. The immunoassay method according to claim 1, wherein the solid phase is chromium-sputtered glass.

14. The immunoassay method according to claim 3, wherein the surface concentrations of analyte are between 0.01 and 5 $ng/cm^2$.

15. The kit according to claim 15, wherein said solid phase is silicon.

16. The immunoassay method of claim 5, wherein the uniform-accessible surface is a rotating disk.

17. The immunoassay method according to claim 1, wherein an antibody binds the analyte to the solid phase.

18. The immunoassay method according to claim 1, wherein an antibody attaches the marker to the analyte.

* * * * *